United States Patent [19]

Stephenson et al.

[11] Patent Number: 4,681,840
[45] Date of Patent: Jul. 21, 1987

[54] DEOXYRIBONUCLEIC ACID MOLECULES USEFUL AS PROBES FOR DETECTING ONCOGENES INCORPORATED INTO CHROMOSOMAL DNA

[75] Inventors: John R. Stephenson, East Norwich; John Groffen; Nora Heisterkamp, both of Westbury, all of N.Y.

[73] Assignee: The United States of America as represented by the Secretary of Commerce, Washington, D.C.

[21] Appl. No.: 571,911

[22] Filed: Jan. 18, 1984

[51] Int. Cl.$^4$ .................... G01N 33/48; G01N 33/52; C12Q 1/68
[52] U.S. Cl. ........................................ 435/6; 435/91; 435/172.3; 436/504; 536/27; 935/78
[58] Field of Search ............... 435/6, 91; 436/94, 504, 436/813; 536/27; 935/78

[56] References Cited

U.S. PATENT DOCUMENTS 4,490,472 12/1984 Gottlieb ............................. 435/6 X
4,535,058 8/1985 Weinberg ......................... 935/78 X

OTHER PUBLICATIONS

Taub, R. et al., Cell, 36, 339-348 (1984).
Sheer, D. et al., Proc. Natl. Acad. Sci. USA, 80, 5007-5011 (1983).
Tsujimoto, Y. et al., Science, 224, 1403-1406 (Jun. 29, 1984).
Tsujimoto, Y. et al., Science, 226, 1098-1099 (Nov. 30, 1984).
Tsujimoto, Y. et al., Nature, 315, 340-343 (May 1985).
Tsujimoto, Y. et al., Science, 228, 1440-1443 (Jun. 21, 1985).
Yunis, J. J., Science, 221, 227-235 (Jul. 15, 1983).
Adams, J. M. et al., Proc. Natl. Acad. Sci. USA, 80, 1982-1986 (Apr. 1983).
Erikson, J. et al., Proc. Natl. Acad. Sci. USA, 80, 820-824 (Feb. 1983).
Erikson, J. et al., Proc. Natl. Acad. Sci. USA, 79, 5611-5615 (Sep. 1982).
Rowley, J. D., Nature, 243, 290-293 (Jun. 1, 1973).
Rowley, J. D., Science, 216, 749-751 (May 14, 1982).
Heisterkamp, N. et al., J. Molecular and Applied Genetics, 2, 57-68 (1983).
Heisterkamp, N. et al., Nature, 299, 747-749, (Oct. 21, 1982).
de Klein, A. et al., Nature, 300, 765-767 (Dec. 1982).
R. Dalla-Favera et al., Proc. Natl. Acad. Sci. USA, 79(24), 7824-7827 (1982).
R. Dalla-Favera et al., Science, 219 (4587), 963-967 (1983).
N. Heisterkamp et al., Nature, 306 (5940), 239-242 (1983).
Chemical Abstracts, 99:188847c (1983).
J. Groffen et al., Cell, 36(1), 93-99 (Jan. 1984).
C. M. Croce et al., Scientific American, 252(3), 54-60 (1985).

Primary Examiner—Sidney Marantz
Attorney, Agent, or Firm—John P. White

[57] ABSTRACT

A single-stranded deoxyribonucleic acid molecule having a length of less than about 25 kb comprises at least three distinct nucleotide sequences which are the sites for incorporation into a chromosome of a deoxyribonucleic acid molecule encoding a deleterious gene. Deoxyribonucleic acid probes have been prepared from such molecules and are useful as hybridization probes for detecting chromosomal deoxyribonucleic acid which has a deoxyribonucleic acid molecule encoding a deleterious gene, i.e. oncogene, incorporated therein.

A single-stranded deoxyribonucleic acid molecule derived from human chromosome 22 which is about 5.8 kb in length contains sites for incorporation of a deoxyribonucleic acid molecule encoding the oncogene c-abl derived from human chromosome 9. Deoxyribonucleic acid probes have been prepared from this molecule and used to detect the abnormal Philadelphia chromosome and chronic myelocytic leukemia.

26 Claims, 4 Drawing Figures

DEOXYRIBONUCLEIC ACID MOLECULES USEFUL AS PROBES FOR DETECTING ONCOGENES INCORPORATED INTO CHROMOSOMAL DNA

BACKGROUND OF THE INVENTION

Throughout this application various publications are referenced by the names of the authors and the year of publication within parentheses. Full citations for these publications may be found at the end of the specification immediately preceding the claims. The disclosures of these publications in their entireties are hereby incorporated by reference into this application in order to more fully describe the state of the art to which this invention pertains.

Certain specific chromosomal translocations are known to be associated with human cancer (for a review see Yunis, 1983). The chromosomal rearrangements that occur as a result of these translocations may activate human cellular oncogenes that have been rearranged. Past studies of these cancers and the chromosomal translocations involved have focused on an analysis of the translocated oncogene sequences themselves.

This invention takes a novel approach in that it uses probes isolated from a limited region of the receptor chromosome which does not normally contain the deleterious gene. This limited region for which we propose the term "breakpoint cluster region" is a deoxyribonucleic acid molecule of limited length within which the various chromosomal breakpoints are clustered. Probes isolated from this region are used to detect a translocation by hybridizing the probes with chromosomal DNA and examining the resulting restriction patterns. Previous studies have identified breakpoints on the chromosomes involved in other cancers (Dalla-Favera et al., 1983; Adams et al., 1983; Erikson et al., 1983; Erikson et al. 1982). However, these breakpoints are distributed over a relatively large region of DNA and thus are not useful as hybridization probes to test for chromosomal translocations.

The breakpoint cluster region on human chromosome 22, which is involved in the formation of the Philadelphia chromosome, is the first such region to be discovered. It is contemplated that such regions exist on other human chromosomes and that this invention will be effective in detecting other diseases evidenced by chromosomal translocations.

Chronic myelocytic leukemia (CML) is characterized by the presence of the Philadelphia (Ph') chromosome in the leukemic cells of 96% of all CML patients. The Ph' chromosome is the result of a translocation between chromosome 22 and chromosome 9 (Rowley, 1973, 1982; Sanberg, 1980); its presence has important prognostic and diagnostic value. Previously we described the localization of the human c-abl oncogene (Heisterkamp et al., 1983a), to chromosome 9 (Heisterkamp et al., 1982) and demonstrated its translocation to the Philadelphia (22q−) chromosome in CML (de Klein et al., 1982). This demonstrated unequivocally that the t(9;22) is reciprocal. As the breakpoint on chromosome 9 is at the most telomeric band on this chromosome, q34, human c-abl must be translocated on a relatively small fragment (less than 5000 kb) to chromosome 22, suggesting a potential role for the c-abl oncogene in CML. This hypothesis was strengthened by the isolation of a chimeric DNA fragment from one CML patient containing sequences from chromosome 9 and 22 and located 14 kb immediately 5' of human v-abl homologous sequences (Heisterkamp et al., 1983b). We have used the chromosome 22-specific sequences of the chimeric DNA fragment to isolate a second chimeric chromosome 9/22 (9q+) fragment from a different CML patient. The chromosome 9-specific sequences in this fragment must be localized at a minimal distance of 40 kb from the human v-abl homologous sequences. Using the same probe, we have isolated an extended region on chromosome 22 from non-CML human DNA. In contrast to the situation on chromosome 9, the breakpoints on chromosome 22 in the DNAs of these two CML patients had occurred in the same region, although not at an identical site. We investigated the genomic organization of this area in a number of other Ph'-positive CML patients: all exhibited abnormal restriction enzyme patterns, indicating that in Ph-positive CML a breakpoint occurs in a single well defined region (less than 5.8 kb in length) of chromosome 22.

SUMMARY OF THE INVENTION

This invention relates to a single-stranded deoxyribonucleic acid molecule having a length less than about 25 kb and preferably less than about 15 kb, and containing at least three distinct nucleotide sequences which are the sites for incorporation into a chromosome of a deoxyribonucleic acid molecule encoding a deleterious gene. Such a single-stranded deoxyribonucleic acid molecule may be derived from a chromosome. The single-stranded molecule may be incorporated into double-stranded deoxyribonucleic acid molecules. Such deleterious genes include oncogenes.

Deoxyribonucleic acid probes, labelled with a detectable marker, have been prepared from such molecules or fragments thereof. Such hybridization probes have diagnostic value and are useful for detecting chromosomal deoxyribonucleic acid which has a deoxyribonucleic acid molecule encoding a deleterious gene incorporated therein.

A specific embodiment of the invention relates to a single-stranded deoxyribonucleic acid molecule derived from human chromosome 22, which is about 5.8 kb in length and contains sites for incorporation of a deoxyribonucleic acid molecule encoding the oncogene c-abl derived from human chromosome 9. Labelled deoxyribonucleic acid probes have been prepared from this molecule and used to detect the abnormal Philadelphia chromosome associated with chronic myelocytic leukemia.

BRIEF DESCRIPTION OF THE FIGURES

In FIG. 1A the human v-abl homologous regions are designated I through VII and are indicated by solid bars; Eco R1 sites are marked by small vertical lines. The vertical arrow points to the breakpoint in the DNA. FIG. 1B shows the molecularly cloned region of DNA of patient 0319129 that contains a breakpoint. The solid bar indicates sequences from chromosome 9, while the open bar indicates sequences from chromosome 22. The 1.2 kb HBg probe is indicated as a hatched box. Restriction enzymes include: Bam HI(B), Bgl II(Bg), Hind III (H), Sst I(S), Xba I (Xb), Xho I (Xh) and Eco RI(E).

FIG. 2A is a restriction enzyme map of the cloned region in which chromosomal breaks occur on chromosome 22. FIG. 2B is a subclone containing the 5.0 kb Bgl II fragment. FIG. 2C is the 6.0 kb Bgl II restriction enzyme fragment and FIG. 2D is the 11.3 kb restriction enzyme fragment of the 9q+ chromosome. Heavy lines indicate sequences from chromosome 22, whereas light lines indicate sequences from chromosome 9. Restriction enzyme include: Bam HI (B), Bgl II (Bg), BstE II (Bs) Eco RI (E), Hind III (H), Kpn I (K), Sst I (S), Xba I (X) and Xho I (Xh).

DETAILED DESCRIPTION OF THE INVENTION

Figure 1:
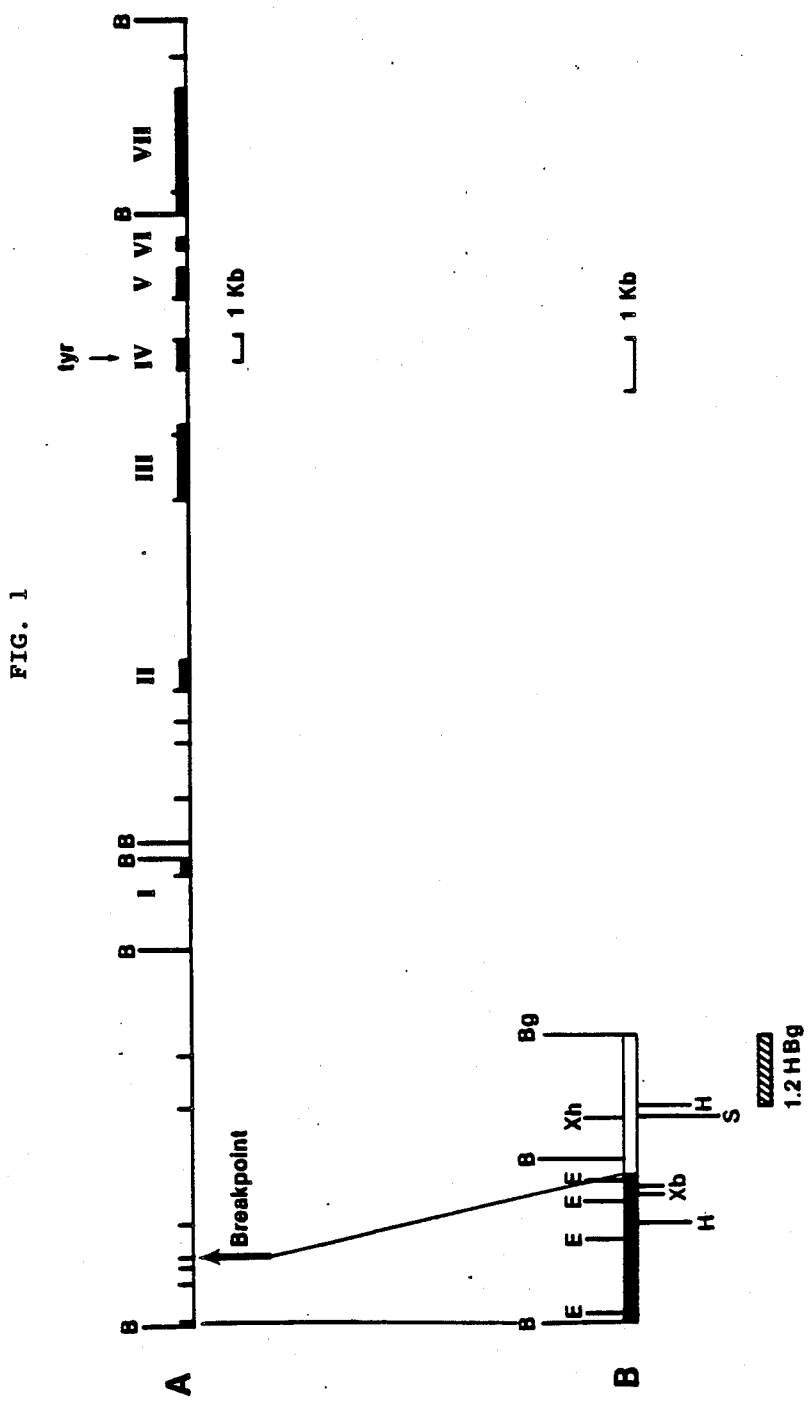
FIG. 1 shows the position of the 9q+ chromosomal breakpoint in spleen DNA of patient 0319129 in relation to human v-abl homologous sequences.

A single-stranded deoxyribonucleic acid molecule having a length less than about 25 kb, preferably a length less than about 15 kb, and containing at least three distinct nucleotide sequences which are sites for incorporation into a chromosome of a deoxyribonucleic acid molecule encoding a deleterious gene has been discovered. Such a single-stranded deoxyribonucleic acid molecule may be derived from a chromosome, e.g. a human chromosome, or may be chemically or enzymatically synthesized. It may also be incorporated into a double-stranded deoxyribonucleic acid molecule.

In certain embodiments of the invention sites for incorporation are breakpoint sites on the chromosome to which a deoxyribonucleic acid molecule encoding a deleterious gene derived from a second chromosome or a distal region of the same chromosome, attaches during a translocation.

Examples of deleterious genes include oncogenes, e.g. c-abl, the activation of which can cause cancer, or other normally innocuous genes which upon activation can cause specific human diseases. In humans the Philadelphia translocation involves the translocation of the oncogene c-abl located on chromosome 9 to chromosome 22 and its incorporation therein. A single-stranded deoxyribonucleic acid molecule derived from chromosome 22 has been discovered which is about 5.8 kb in length and contains breakpoint sites which are the incorporation sites at which the deoxyribonucleic acid molecule encoding the oncogene c-abl derived from chromosome 9 attaches to chromosome 22.

The single-stranded deoxyribonucleic acid molecule or fragments of it, e.g. fragments of such a molecule produced by restriction enzyme cleavage, may be labelled with detectable markers, such as radioactive or fluorescent or enzymatic markers. These labelled molecules may then be used as hybridization probes to detect a chromosomal deoxyribonucleic acid molecule containing a deoxyribonucleic acid molecule encoding a deleterious gene incorporated therein. Certain embodiments of this invention involve the use of such fragments prepared by the cleavage of the 5.8 kb fragment derived from human chromosome 22 containing the sites for incorporation of the deoxyribonucleic acid molecule encoding the oncogene c-abl derived from human chromosome 9. Cleavage of this molecule with the restriction enzymes Hind III and Bgl II yielded a 1.2 kb fragment while cleavage with Hind III and Bam HI yielded a 0.6 kb fragment. Both of these fragments were labelled with radioactive nucleotides and used as probes.

A method of detecting chromosomal deoxyribonucleic acid containing a deoxyribonucleic acid molecule encoding a deleterious gene incorporated therein comprises treating total chromosomal deoxyribonucleic acid under suitable denaturing conditions to obtain single-stranded deoxyribonucleic acid molecules. These single-stranded molecules may then be contacted with a labelled probe which is a single-stranded deoxyribonucleic acid molecule or a fragment of such a molecule, which includes sites for the incorporation of the deleterious gene, under suitable conditions permitting hybridization of complementary single-stranded molecules. The hybridized molecules may then be identified or separated to thereby detect deoxyribonucleic acid containing the deleterious gene.

Another method of detecting a chromosomal deoxyribonucleic acid molecule containing a deoxyribonucleic acid molecule encoding a deleterious gene incorporated therein comprises cleaving the chromosomal deoxyribonucleic acid with the appropriate restriction enzymes, and then separating the fragments by gel electrophoresis. The separated fragments may be denatured to obtain single-stranded deoxyribonucleic acid molecules which may be recovered from the gel and immobilized on a suitable solid support, e.g. a nitrocellulose filter. The immobilized single-stranded fragments may then be contacted with a labelled deoxyribonucleic acid probe which is a single-stranded deoxyribonucleic acid molecule or a fragment of such a molecule, which includes sites for the incorporation of the deleterious gene under suitable conditions permitting hybridization of complementary single-stranded molecules. The hybridized molecules so formed may then be detected e.g. by autoradiography, and abnormalities in the restriction patterns of the chromosomal deoxyribonucleic acid resulting from the incorporation of deoxyribonucleic acid encoding the deleterious gene may be identified.

A specific embodiment of this invention relates to a method of diagnosing chronic myelocytic leukemia in a human subject. This leukemia is associated with the abnormal Philadelphia chromosome which contains the translocated oncogene c-abl. Chromosomal deoxyribonucleic acid is digested with the appropriate restriction enzymes, e.g. Hind III, Bam HI or Bgl II. The resulting fragments are separated by gel electrophoresis, denatured under suitable conditions to obtain single-stranded deoxyribonucleic acid molecules, recovered from the gel and immobilized on a suitable solid support such as a nitrocellulose filter. The immobilized single-stranded fragments are then contacted with a labelled probe, e.g. a radioactivity-labelled single-stranded deoxyribonucleic acid molecule isolated from the 5.8 kb region of chromosome 22 which includes sites for the incorporation of the oncogene c-abl derived from chromosome 9, such as the 1.2 kb Hind III, Bgl II fragment or the 0.6 kb Hind III, Bam HI fragment, under suitable conditions permitting hybridization of complementary single-stranded molecules. The hybridized molecules so formed may then be detected, e.g. by autoradiography, and abnormalities in the restriction patterns of the chromosomal deoxyribonucleic acid caused by the presence of the abnormal Philadelphia chromosome may be identified.

Although the invention is specifically described with respect to the use of single-stranded deoxyribonucleic acid molecules as probes, one of ordinary skill in the art would understand that a ribonucleic acid molecule having a sequence complementary to that of the single-stranded deoxyribonucleic acid molecule could also be used as a hybridization probe. Methods for preparing such ribonucleic acid molecules are known to those skilled in the art and include preparing the molecule by reverse transcription of the deoxyribonucleic acid molecule.

EXPERIMENTAL DETAILS

Experimental Procedures

Somatic Cell Hybrids

PgME-25 Nu is a human-mouse somatic cell hybrid obtained from fusion with mouse Pg19 cells; it contains as its only human component chromosome 22. Chinese hamster cell line E36 was used to obtain hybrids 10CB-23B and 14CB-21A. The hybrid 10CB-23B contains human chromosomes 5, 9, 11, and 19, whereas 14CB-21A has retained chromosomes 4, 7, 8, 14, 20, and 9q+ (Geurts van Kessel et al., 1981b; Geurts Van Kessel et al., 1981C; de Klein et al., 1983). WESP 2A was obtained by fusion of mouse WEHI-3B cells with leukocytes of a Ph'-positive CML patient and contains human chromosomes 7, 8, and 14 in addition to the Ph' chromosome (de Klein et al., 1983).

Southern Blot Analysis

High molecular weight DNAs were isolated as described (Jeffreys and Flavell, 1977), digested with restriction enzymes, and electrophoresed on agarose gels. Blotting was according to Southern (1975) on nitrocellulose (Schleicher and Schuell, pH 7.9). Nick translation of probes and filter hybridizations were as described (Flavell et al., 1978, Bernards and Flavell, 1980). Specific activity of the probes were $2-5 \times 10^8$ cpm/µg. Filters were exposed to XAR-2 film (Kodak) at $-70°$ C. with Dupont Lightning Plus intensifying screens.

Isolation of Probes

DNA probes were prepared by digestion with appropriate restriction enzymes, followed by electrophoresis through low-melting point agarose gels. Desired bands were cut from the gel and brought into solution by heating at 65° C. for 30 min. Agarose was removed by two extractions with phenol equilibrated with 0.3M NaOAc (pH 5.0), and one extraction with phenol/chloroform/isoamyl alcohol (25:24:1). DNA was precipitated with ethanol and 0.2M NaOAc (pH 4.8) in the presence of 20 µg/ml Dextran T-500 as carrier. Restriction enzymes and low melting point agarose were purchased from Bethesda Research Laboratories and were used according to the supplier's specifications.

Molecular Cloning

Subcloning of the 5.0 kb Bgl II fragment and cloning of the 11.3 kb Bam H1 fragment was according to published procedures (Groffen et al., 1983b). A previously described (Groffen et al., 1982) human lung carcinoma cosmid library was screened with the 1.2 HBg probe according to the method of Grosveld et al. (1981). Three positive cosmid clones were isolated and mapped independently by digestion of individual restriction enzyme fragments isolated from low melting point agarose gels.

Chromosomal DNA From CML Patients

DNAs analyzed include isolates from CML patient frozen spleens; 02120185, 0311068, 031929, 7701C, C999, C481, C080, C011; blood, H80-251, CML O, H81-164, H81-122, H81-118, H79-179, H77-94, H81-258, H79-147; bone marrow B79-216, B79-100; and human cell lines GM 3314 and A204. CML patients 0311068 and 7701C contained a very high percentage of leukemic cells: the percentage leukemic cells in other spleen tissues is not known. There are no data concerning the presence of the Ph' chromosome in these spleen cells. Blood and bone marrow cells of all patients except H79-147 were Ph' positive. DNA isolates from fibroblasts of patient H80-257 and fibroblast cell line AG 1732 were also studied. AG1732 was obtained from the Human Genetic Mutant Cell Repository (Camden, NJ.) and was established from a CML patient carrying the Ph' chromosome in her leukemic cells. Frozen spleen tissues were obtained through the Biological Carcinogenesis Branch, DCCP.

Results

Isolation of a 9q+ Chimeric Fragment

Previously we have isolated a chimeric DNA fragment containing sequences originating from chromosomes 9 and 22 (FIG. 1B) from a CML patient, 0319129. On chromosome 9, the breakpoint was located immediately to the 5' of human v-abl homologous sequences (FIG. 1A) and may even be within the human c-abl oncogene. However, the DNAs of two other CML patients did not contain rearrangements in this region; furthermore, we have molecularly cloned an additional 11 kb of DNA to the 5' and have found no rearrangements in this area for these two DNAs. We investigated whether we could localize the Ph' translocation breakpoint to a specific site on chromosome 22. Using a 1.2 kb Hind III-Bgl II fragment (1.2HBg, see FIG. 1B) containing chromosome 22 sequences from the breakpoint region of CML patient 0319129 as a probe, we examined the DNA of the leukemic cells of a second patient (02120185). This probe detects a normal 5.0 kb Bgl II fragment in control DNA, in DNA of patient 0319129 and in DNA of patient 02120185. As expected, it also detects the breakpoint fragment of DNA 0319129 (FIG. 1B). In DNA of patient 02120185, an extra Bgl II fragment of 6.6 kb is visible. Similarly, this probe hybridizes to a normal 3.3 kb Bam H1 fragment in all three DNAs, but detects an additional abnormal 11.3 kb Bam H1 fragment in DNA 02120185. As we could detect additional restriction enzyme fragments with other restriction enzymes in DNA 02120185, we examined whether these abnormal fragments were the result of the presence of a chromosomal breakpoint. Using the 1.2 kb HBg fragment as a probe, we molecularly cloned the 11.3 kb Bam H1 fragment in charon 30. In this fragment only 1.2 kb of DNA, homologous to the probe, was defined as originating from chromosome 22. To determine all chromosome 22-specific sequences in the 11.3 kb Bam H1 fragment, it was necessary to isolate the homologous region on chromosome 22 from non-CML DNA. For this purpose, a previously described (Groffen et al., 1982) human lung carcinoma cosmid library was screened with the 1.2 kb HBg probe. Three cosmid clones were isolated, which contained overlapping portions of the same region.

Molecular Cloning of Ph' Breakpoint Region of Normal Chromosome 22

Figure 2:
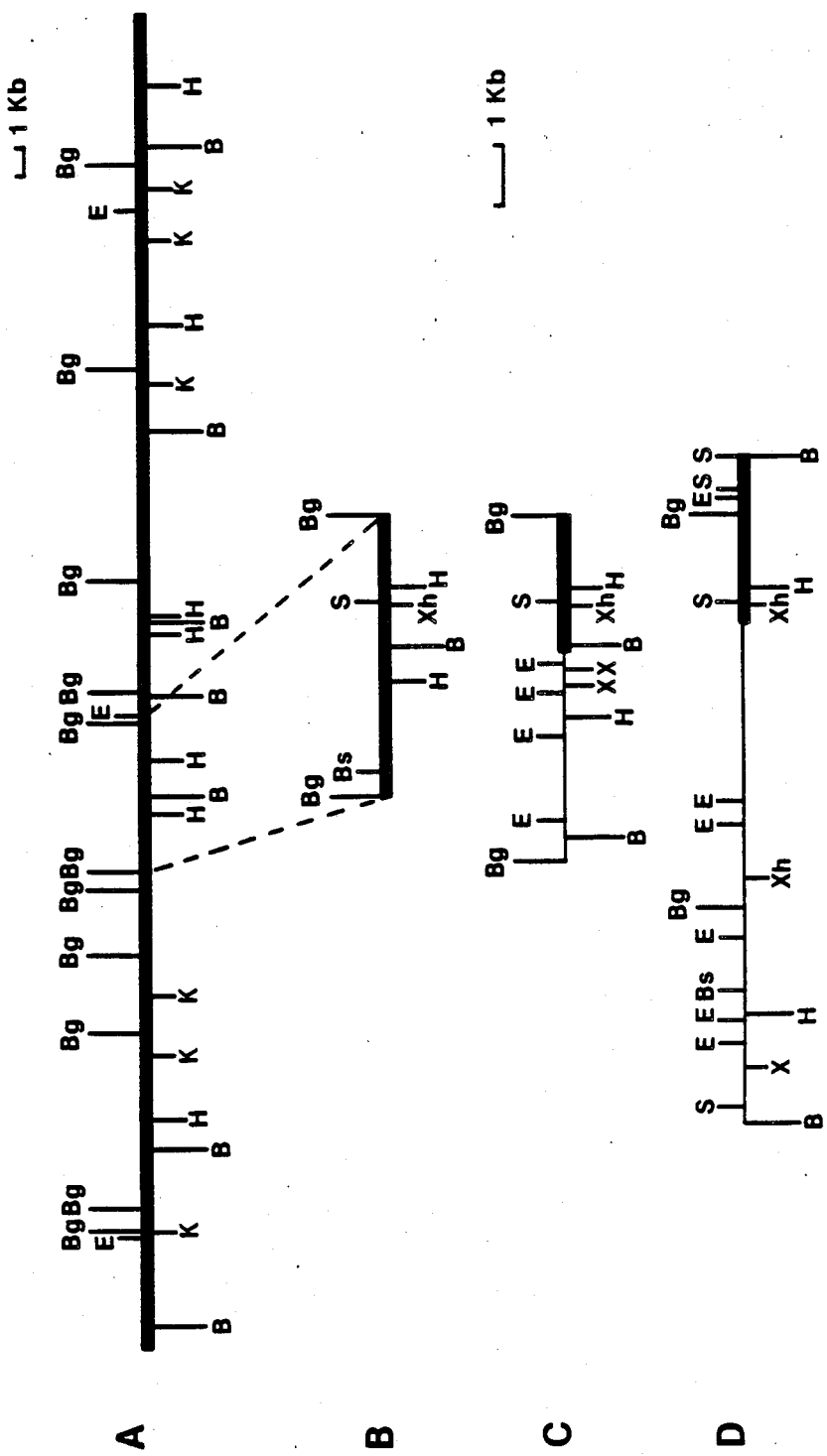
FIG. 2 shows a comparative restriction enzyme analysis of the breakpoint region on chromosome 22 with two 9q+ breakpoint regions.

As shown in FIG. 2A, a region of approximately 46 kb was molecularly cloned; the 1.2 kb HBg probe hybridizes to a Bgl II fragment of 5.0 kb, located centrally in the cloned region. No homology is apparent between the restriction map of this region and that of human c-sis (Dalla-Favera et al., 1981), an oncogene situated on chromosome 22 but translocated to chromosome 9 in the Ph' translocation (Groffen et al., 1983a). This confirms earlier reports that indicated that c-sis is not located in the immediate proximity of the Ph'breakpoint (Bartram et al., 1983a). In variant Burkitt lymphoma, a t(8;22) has been described in which the immunoglobulin light chain was found to be involved (de la Chapelle et al., 1983). The light-chain constant region (Cλ) and the Ph' chromosomal breakpoint have been localized to chromosome 22 band q11 (Rowley, 1973; McBride et al., 1982; Yunis, 1983); this suggests that c-abl could be translocated into Cλ in patients with CML. However, a probe isolated from the λ constant region showed no cross-homology with the above-described chromosome 22 sequences. Additionally, no hybridization to a murine λ-variable region probe (Miller et al., 1981) was observed.

To facilitate comparison of the 11.3 kb Bam H1 fragment with homologous sequences on chromosome 22, the 5.0 kb Bgl II fragment was subcloned into pSV2-neo (FIG. 2B). In concordance with our previous results (Heisterkamp et al., 1983b), in the 6.0 kb Bgl II breakpoint fragment from CML patient 0319129, restriction enzyme sites 3' to the most 3' Eco R1 site originate from chromosome 22 (FIG. 2C). In the 11.3 kb Bam H1 fragment (FIG. 2D) approximately 2.5 kb of DNA, including the 3' Bam H1 site and extending to the 3' Xho 1 site, originates from chromosome 22.

The 11.3 kb Bam H1 Fragment Also Contains a Breakpoint

To establish conclusively that the 11.3 kb Bam H1 fragment represents a chimeric fragment of chromosomes 22 and 9, we isolated a 1.3 kb Eco R1 fragment from the chromosome 22 nonhomologous region. Using this fragment as a probe, homologous sequences were detected in Bgl II-digested mouse DNA and Chinese hamster DNA. These bands, however, were clearly resolved from the Bgl II fragment visible in human DNA. No human sequences homologous to the probe were detected in rodent-human somatic cell hybrids PgMe-25Nu, having human chromosome 22 as its only human component or in WESP-2A, containing a Ph' chromosome but not chromosome 9 or 9q+ (de Klein et al., 1982). In the rodent-human somatic cell hybrids 10CB-23B, containing human chromosome 9 and in 14CB-21A, containing a 9q+ chromosome, a Bgl II fragment of human origin homologous to the probe was clearly present. The only human DNA sequences these two hybrids have in common are those originating from chromosome 9. Therefore the 11.3 kb Bam H1 fragment possesses a breakpoint and represents a chimeric fragment containing chromosome 9- and 22-specific sequences isolated from a second CML patient.

Clustering of Ph' Breakpoints on Chromosome 22 in CML Patients

Since in each of the above two CML DNAs the breakpoint in the t(9;22) on chromosome 22 was localized within a common region, we decided to investigate this area in other CML DNAs. As the 1.2 HBg probe had detected abnormal (9q+) Bgl II restriction fragments in DNAs 0319129 and 02120185, we subjected 17 additional independent CML DNAs to similar analysis; six of these were from spleen tissue, nine were from patient blood, and two were from bone marrow. CML DNAs from spleen, blood, and bone marrow of patients 0311068, 7701C, C999, C481, B79-100, B79-216, H80-251, CML O, H81-164, H81-118 H79-179, H77-94 and H81-122 all contained additional Bgl II fragments hybridizing to the 1.2 HBg probe. The DNAs of the patients H81-258, CO80, C011 and H 79-147 did not exhibit abnormal Bgl II fragments. Two of these H81-258, and CO80, showed deviant restriction enzyme patterns with other restriction enzymes (this will be discussed below).

To confirm that the 1.2 HBg probe detected chromosomal rearrangements and not merely DNA polymorphisms for the restriction enzyme Bgl II, all DNAs were subjected to digestion with at least one, but in most cases two or more different restriction enzymes. After hybridization with the 1.2 HBg probe, abnormal restriction enzyme fragments were detected in all Ph'-positive CML DNAs (also see below). Therefore, a polymorphism for Bgl II seems an unlikely explanation for the abnormal fragments, moreover, in the DNAs of most patients, abnormal fragments of different molecular weights are detected with the 1.2 HBg probe.

No extra Bgl II fragments were found in DNA isolated from cultured fibroblasts of patient H80-251 although an extra Bgl II fragment is clearly visible in DNA isolated from the leukemic cells of this patient. Moreover, DNA isolated from the fibroblast cell line, AG 1732, established from a Ph'-positive CML patient, also lacked abnormalities in this region. Finally, in DNA isolated from leukemic cells of a Ph'-negative CML patient (H79-147) and of a two-year old child with juvenile Ph'-negative CML, (CO11), no visible rearrangements were found confirming our results of previous experiments (Bartram et al., 1983b) in which no translocations concerning c-abl to chromosome 22 or c-sis to chromosome 9 were found in Ph'-negative CML.

Sublocalization of Ph' Breakpoints on Chromosome 22

As is apparent from the detailed restriction enzyme analysis of the breakpoint fragments of the DNAs of patients 0319129 and 02120185, the exact breakpoints are not localized at identical sites on chromosome 22. To sublocalize the breakpoints in the DNAs of the other CML patients more precisely, we arbitrarily divided the 5.0 kb Bgl II fragment into segments bordered by restriction enzyme sites for Bgl II, Bam H1 and Hind III (see FIG. 3). Region 0 thus extends from the 5' Bgl II site to the first 5' Hind III site, region 1, a 0.6 kb Hind III -Bam HI fragment, is bordered by the same Hind III site at the 5' and a Bam H1 site 3' to it. Region 2 is delineated by this Bam H1 site at the 5' and a Hind III site 3' to it; region 3 is the 1.2 kb Hind III-Bgl II fragment (1.2 HBg) used as a probe in the experiments described above. Region 4 is outside the 5.0 kb Bgl II fragment and is bordered at the 5' by the Bgl II site and at the 3' by the Bam H1 site.

As is evident from the restriction enzyme map of the 6.0 kb breakpoint fragment of CML DNA 0319129 (FIG. 2C), the Bam H1 site from chromosome 22 in region 1 is found on the 9q+ chromosome, whereas the Hind III site 5' to it is missing; therefore, a break must have occurred between these two restriction enzyme sites in region 1. In accordance with this, only a (normal) 3.3 kb Bam H1 fragment is detected with the 1.2 HBg probe, which originates from a region 3' to the Bam H1 site. In DNA 02120185, however, this Bam H1 site is missing on the 9q+ chromosome (FIG. 2D) and, therefore the 1.2 HBg probe detects, in addition to the normal 3.3 kb Bam H1 fragment, the 11.3 chimeric Bam H1 fragment. As the 3' Hind III site at region 2 is present in this 9q+ fragment, the breakpoint in this DNA is in region 2.

In DNA 0311068, as in DNA 0319129, only a normal 3.3 kb Bam H1 fragment is detected with the 1.2 HBg probe, indicating that no break has occurred within this fragment. When the 0.6 kb Hind III-Bam H1 fragment encompassing region 1 is used as a molecular probe, a normal 5.0 kb and two abnormal Bgl II fragments of 4.0 and 3.2 kb are visible. The 3.2 kb Bgl fragment represents a 9q+ chimeric fragment containing the 3' Bgl II site from the 5.0 kb Bgl II fragment on chromosome 22, it is also detected with the 1.2 HBg probe. The 4.0 kb Bgl II fragment is a 22q− chimeric fragment with the 5' Bgl II site originating from chromosome 22; it is not detected by the 1.2 HBg probe. The breakpoint in DNA 0311068 must be located in region 1.

The 1.2 HBg probe detects, in addition to a normal 3.3 kb Bam H1 fragment, an abnormal 6.2 kb Bam H1 fragment in CML DNA 7701C. The Bam H1 site bordering region 2 at the 5' must, therefore, be absent from the 9q+ chromosome. The Hind III site at the 3' of region 2 has been retained, as only one normal 4.5 kb Hind III fragment is visible after hybridization to 1.2 HBg. This CML DNA must contain a breakpoint in region 2.

Patient C481 and H77-92 apparently have a breakpoint in region 3, encompassing the 1.2 HBg probe. For example, in DNA of patient C481 the 1.2 HBg probe hybridizes to three restriction enzyme fragments in every restriction enzyme digest; abnormal Bgl II fragments of 6.0 and 2.8 kb and a normal one of 5.0 kb, abnormal Hind III fragments of 7.0 and 3.5 kb in addition to a normal 4.5 kb fragment abnormal Bam H1 fragments of 7.5 and 5.2 kb and a normal 3.3 kb fragment. Therefore, in this CML, DNA the 1.2 HBg probe detects both the 22q− and 9q+ breakpoint fragments.

The situation in the DNA of patient CO80 is less clear. As only one normal 5.0 kb Bgl II fragment is visible after hybridization to 1.2 HBg a chromosomal breakpoint most likely has occurred outside the Bgl II fragment. As the 1.2 HBg probe detects an abnormal 5.0 kb Hind III fragment in addition to the normal 4.5 kb Hind III fragment, a chromosomal breakpoint may be situated immediately 3' of the 5.0 kb Bgl II fragment. This is supported by the hybridization of the same probe to an abnormal 13 kb Bam H1 fragment (and the normal 3.3 kb fragment). The breakpoint has therefore been tentatively placed in region 4, in DNA of this patient, the 1.2 HBg probe would detect only 22q− restriction enzyme fragments.

Using different restriction enzymes and probes from the 5.0 kb Bgl II fragment, we have analyzed the location of the breakpoint in the CML DNAs studied. These results are summarized in Table 1.

TABLE 1

Breakpoint Location within bcr of Ph'-positive CML Patients

| CML Patient | Breakpoint Location | CML Patient | Breakpoint Location |
|---|---|---|---|
| 0311068 | 1 | H81-122 | 2, 3 |
| 7701C | 2 | H81-118 | 2, 3 |
| C999 | 1 | H79-179 | 1 |
| C481 | 3 | H77-94 | 3 |
| B79-216 | 0, 1, 2 | C080 | 4 |
| H80-251 | 0, 1 | 0319129 | 1 |
| CML O | 2 | 02120185 | 2 |
| H81-164 | 2, 3 | H81-258 | 1, 2 |
| B79-100 | 2 | | |

Figure 3:
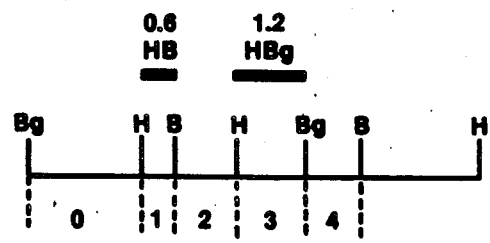
FIG. 3 shows a schematic diagram of the region within the cloned chromosome 22 sequences containing Ph' translocation breakpoints that have been identified. The probes used are indicated.

The different breakpoint subregions (0-4) are as indicated in FIG. 3. For some patients, the exact breakpoint subregion has not yet been determined more than one subregion is indicated for these patients in the table.

DISCUSSION

In the present studies we have identified and cloned a breakpoint cluster region (bcr) on chromosome 22, involved in the chromosomal translocation, t(9;22), of Ph' positive CML. In total we have studied 19 CML patients, ten of these were shown to be Ph'-positive by cytogenetical analysis. All of the patients of this latter group possessed a chromosomal break within bcr. Of the remaining nine patients, one was cytogenetically characterized as Ph'-negative and a second patient has Ph'-negative juvenile CML; as expected, they did not exhibit a breakpoint in this region. Seven of seven non-karyotyped patients were Ph'-positive because a chromosomal break could be identified within bcr. The involvement of bcr in the Ph' translocation is highly specific for CML, as analogous rearrangements were not found in DNAs isolated from other neoplastic tissues or cell lines, including DNAs from four acute myeloid leukemia patients, one acute myelomonocytic leukemia patient, glioblastoma, melanoma, multiple myeloma and teratocarcinoma cell lines. A low percentage of acute lymphocytic leukemia patients do however, also exhibit the Ph' translocation. Since abnormalities were not seen in a fibroblast cell line established from a Ph'-positive CML patient, in cultured fibroblasts of a Ph'-positive CML patient, leukemic cells of two Ph'-negative CML patients, we believe these rearrangements to be highly specific for the leukemic cells in Ph'-positive CML patients. In two patients these rearrangements were rigorously analyzed and shown to represent chromosomal breakpoints. Probes, isolated from the bcr, in particular the 1.2 kb HBg probe, are highly specific tools for the identification of the Ph' translocation in leukemic DNA and as such, may be of diagnostic value, in particular when no metaphase chromosome spreads are obtainable.

Figure 4:
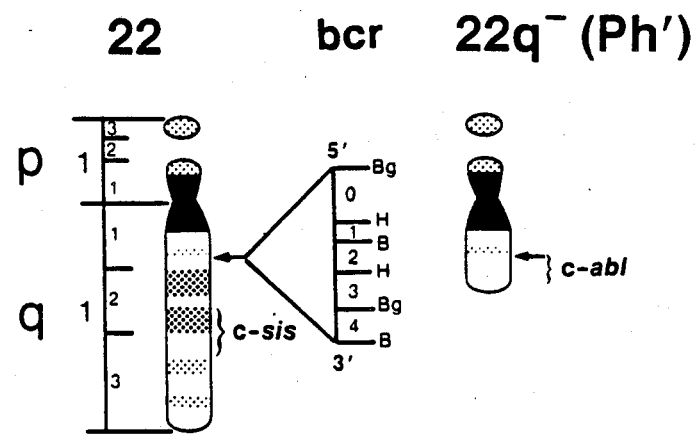
FIG. 4 shows a diagramatic representation of the Ph' translocation. Horizontal arrows indicate the breakpoint in chromosome 22. The maximum size of the bcr is 5.8 kb.

We have molecularly cloned the region of chromosome 22 from non-CML DNA that contains the Ph' breakpoints in CML DNA. The orientation of the chromosome 22 specific sequences in the two 9q+ breakpoint fragments determines the orientation of the breakpoint cluster region on the chromosome: the most 5' end will remain on chromosome 22 (FIG. 4) and, depending on the exact position of a breakpoint, a smaller or larger region of bcr will be translocated to chromosome 9. Although the breakpoint on the Ph' chromosome is in band q11 (Rowley, 1973; Yunis, 1983) and the λlight-chain constant region has been localized to the same band (McBride et al., 1982; our unpublished results) no cross-homology was observed between the chromosome 22 cosmid clones and Cλ. As of yet, these clones contain unidentified sequences. Experiments to determine if this region of chromosome 22 contains protein coding regions and/or enhancer sequences are in progress.

Previously we have reported the isolation of a Ph' breakpoint fragment containing chromosome 9 sequences originating approximately 14 kb 5' of human v-abl homologous sequences (Heisterkamp et al. 1983b). However, we were unable to detect chromosomal breakpoints in other CML DNAs up to 11 kb 5' of this breakpoint. The 9q+ breakpoint fragment from a second CML patient, isolated in the present study, contains 9 kb of DNA originating from chromosome 9. Preliminary results suggest that these sequences must be separated by, at minimum, 27 kb of DNA 5' of the previously reported breakpoint. Therefore, the breakpoint on chromosome 9 appears to be variable in different Ph'-positive CML patients and may be found within a relatively large but limited region on chromosome 9; the region of chromosome 9 containing human c-abl (q34-qter) that is translocated to chromosome 22 is too small to be visualized by cytogenetic, analysis and does not exceed 5000 kb (Heisterkamp et al., 1983b; de Klein et al., 1982). The size of the region over which the chromosome 9 breakpoints are distributed in the Ph' translocation is too large to provide for a diagnostic test by currently available methods.

At present, we do not know whether the two breakpoints we have identified on chromosome 9 actually occur within human c-abl coding sequences since the most 5' exon of human c-abl has not yet been determined. However, the possibility must be considered that the human c-abl oncogene extends over a much larger region than the 3.5 kb region characterized by homology to the viral oncogene v-abl; whereas the v-abl oncogene is 3.5 kb in length (Goff et al., 1980). Homologous RNA species ranging in size from 5-7 kb (Ozanne et. al., 1982; Westin et al., 1982), have been reported in humans. In contrast to the situation on chromosome 9, the breakpoints on chromosome 22 seem to be clustered in a very limited region. It is evident, however, even at the restriction enzyme level, that the breakpoints have not occurred in one specific site but rather are distributed over a region of up to 5.8 kb.

Analogous to the t(9;22) in Ph'-positive CML, a t(8;14) is found in many patients with Burkitt lymphoma: in the latter case, the human oncogene c-myc, located on chromosome 8, (Dalla-Favera et al., 1982; Taub et al., 1982) is often translocated into the immunoglobulin heavy-chain locus on chromosome 14 (Taub et al., 1982; Dalla-Favera et al., 1983; Adams et al., 1983; Erikson et al., 1983; Hamlyn and Rabbits, 1983). The breakpoints on chromosome 8 may be distributed over a relatively large region 5' of human c-myc (Dalla-Favera et al., 1983; Adams et al., 1983; Erikson et al., 1983), a situation analogous to that of human c-abl on chromosome 9. On chromosome 14, breakpoints in the variable (Erikson et al., 1982) and in the constant region of the heavy-chain locus have been reported in Burkitt lymphoma, indicating that neither the breakpoints on chromosome 8 nor those on 14 are localized within a breakpoint cluster as discussed in the present study. The bcr on chromosome 22 seems as of yet to be unique in human. However, the existence of bcrs on other human chromosomes is not unlikely taking into consideration the increasing number of reports of other highly specific translocations in neoplastic diseases (for a review, see Yunis, 1983).

The specificity of the presence of a chromosomal breakpoint on chromosome 22 within bcr in Ph'-positive CML indicates that this region may be involved in CML. Consistent with this possibility is the fact that the bcr on chromosome 22 corresponds to a functionally active human gene which we now know to be expressed at a high level (Heisterkamp et al. unpublished results). Additionally, a human oncogene, c-abl, is consistently translocated to chromosome 22, even in patients with complex Ph' translocations (Bartram et al., 1983b) and is amplified in a CML cell line, K 562,) (Heisterkamp et al., 1983b). Although the breakpoints on chromosome 9 are distributed over a relatively large region of DNA 5' to human v-abl homologous sequences, the specific translocation of this oncogene in the t(9;22) must be of functional significance. Therefore, we believe that both human c-abl and bcr may be associated with the malignancy of Ph'-positive CML.

REFERENCES

Adams, J. M., et al. (1983), Proc. Nat. Acad. Sci. USA 80, 1982–1986.
Bartram, C. R., et al. (1983a), Blood, in press.
Bartram, C. R., et al. (1983b), Nature 306, 277–280.
Bernards, R. and Flavell, R. A. (1980), Nucl. Acids Res 8, 1521–1534.
Dalla-Favera, R., et al. (1981), Nature 292, 31–35.
Dalla-Favera, R., et al. (1982), Proc. Nat. Acad. Sci. USA 79, 7824–2827.
Dalla-Favera, R., et al. (1983), Science 219, 963–967.
de Klein, A., et al. (1982), Nature 300, 765–767.
de la Chapelle, A., et al. (1983), Nucl. Acids Res. 11, 1133–1142.
Erikson, J., et al. (1982), Proc. Nat. Acad. Sci. USA 79, 5611–5615.
Erikson, J., et al. (1983), Proc. Nat. Acad. Sci. USA 80, 820–824.
Flavell, R. A., et al. (1978), Cell 15, 25–41.
Geurts van Kessel, A. H. M., et al. (1981a), Somatic Cell Genet 7, 645–656.
Geurts van Kessel, A. H. M., et al. (1981b), Cytogenet Cell Genet 30, 83–91.
Geurts van Kessel, A. H. M., et al. (1981c), Cancer Genet Cytogenet 6, 55–58.
Goff, S. P., et al. (1980), Cell 22, 777–785.
Groffen J. et al. (1982), Science 216, 1136–1138.
Groffen, J., et al. (1983a), J. Exp. Med. 158, 9–15.
Groffen, J., et al. (1983b), Virology 126, 213–227.
Grosveld, F. G., et al. (1981), Gene 13, 227–237.
Hamlyn, P. H. and Rabbits T. H. (1983), Nature 304, 135–139.
Heisterkamp, N., et al. (1982), Nature 299, 747–749.
Heisterkamp, N., et al. (1983a), J. Mol. App. Genet 2, 57–68.
Heisterkamp, N., et al. (1983b), Nature 306, 239–242.
Jeffreys, A. J. and Flavell, R. A. (1977), Cell 12, 429–439.
McBride, O. W., et al. (1982), J. Exp. Med 155, 1480–1490.
Miller, J., et al. (1981), Proc. Nat. Acad. Sci. USA 78, 3829–3833.
Ozanne, B., et al. (1982)., Nature 299, 744–747.
Rowley, J. D. (1973), Nature 243, 290–293.
Rowley, J. D. (1982), Science 216, 749–751.
Sandberg, A. A. (1980), The Chromosomes in Human Cancer and Leukemia. (New York: Elsevier).
Southern, E. M. (1975), J. Mol. Biol. 98, 503–517.
Taub, R., et al. (1982), Proc. Nat. Acad. Sci. USA 79, 7837–7841.
Westin, E. H., et al. (1982), Proc. Nat. Sci. USA 79, 2490–2494.
Yunis, J. J. (1983), Science 221, 227–236.

What is claimed is:

1. A single-stranded deoxyribonucleic acid molecule having a length less than about 25 kb which comprises at least three distinct nucleotide sequences which are present in a breakpoint cluster region and which are sites for incorporation into a chromosome of a deoxyribonucleic acid molecule encoding an oncogene.

2. A single-stranded deoxyribonucleic acid molecule according to claim 1, which is less than about 15 kb in length.

3. A single-stranded deoxyribonucleic acid molecule according to claim 1, wherein the sites for incorporation are breakpoint sites to which a deoxyribonucleic acid molecule which encodes the oncogene derived from a second chromosome, or a distal region of the same chromosome, attaches during a translocation.

4. A double-stranded deoxyribonucleic acid molecule having a length less than about 25 kb which includes the single-stranded deoxyribonucleic acid molecule of claim 1.

5. A ribonucleic acid molecule which is complementary to the single-stranded deoxyribonucleic acid molecule of claim 1.

6. A single-stranded deoxyribonucleic acid molecule of claim 1, wherein the single-stranded deoxyribonucleic acid molecule is derived from a chromosome.

7. A single-stranded deoxyribonucleic acid molecule according to claim 6 wherein the chromosome is a human chromosome.

8. A fragment of the deoxyribonucleic acid molecule of claim 1 obtained by restriction enzyme cleavage.

9. A fragment of claim 8 labelled with a detectable marker.

10. A method of detecting chromosomal deoxyribonucleic acid containing a deoxyribonucleic acid molecule encoding an omogene incorporated therein which comprises treating total chromosomal deoxyribonucleic acid under denaturing conditions to obtain single-stranded deoxyribonucleic acid molecules, contacting the single-stranded deoxyribonucleic acid molecules so obtained with a deoxyribonucleic acid molecule of claim 9 which includes sites for the incorporation of the oncogene under conditions permitting hybridization of complementary single-stranded molecules and separating hybridized molecules so formed to thereby detect chromosomal deoxyribonucleic acid containing an oncogene.

11. A method of detecting chromosomal deoxyribonucleic acid containing a deoxyribonucleic acid molecule encoding an oncogene incorporated therein which comprises cleaving total chromosomal deoxyribonucleic acid with restriction enzymes under cleaving conditions, separating the fragments so obtained by gel electrophoresis, denaturing the fragments to obtain single-stranded deoxyribonucleic acid molecules, recovering the denatured single-stranded fragments from the gel, immobilizing them on a solid support, contacting the immobilized single-stranded deoxyribonucleic acid fragments with a deoxyribonucleic acid probe of claim 9 which includes sites for the incorporation of the oncogene under conditions permitting hybridization of complementary single-stranded molecules, identifying the hybridized molecules so formed to thereby detect abnormalities in the restriction patterns of the chromosomal deoxyribonucleic acid caused by the incorporation of deoxyribonucleic acid containing the oncogene into the chromosome.

12. A deoxyribonucleic acid molecule of claim 1 labelled with a detectable marker.

13. A deoxyribonucleic acid molecule of claim 12, wherein the marker is radioactive.

14. A deoxyribonucleic acid molecule of claim 12, wherein the marker is fluorescent.

15. A method of detecting chromosomal deoxyribonucleic acid containing a deoxyribonucleic acid molecule encoding an oncogene incorporated therein which comprises treating total chromosomal deoxyribonucleic acid under denaturing conditions to obtain single-stranded deoxyribonucleic acid molecules, contacting the single-stranded deoxyribonucleic acid molecules so obtained with a deoxyribonucleic acid molecule of claim 12 which includes sites for the incorporation of the oncogene under conditions permitting hybridization of complementary single-stranded molecules and separating hybridized molecules so formed to thereby detect chromosomal deoxyribonucleic acid containing an oncogene.

16. A method of detecting chromosomal deoxyribonucleic acid containing a deoxyribonucleic acid molecule encoding an oncogene incorporated therein which comprises cleaving total chromosomal deoxyribonucleic acid with restriction enzymes under cleaving conditions, separating the fragments so obtained by gel electrophoresis, denaturing the fragments to obtain single-stranded deoxyribonucleic acid molecules, recovering the denatured single-stranded fragments from the gel, immobilizing the fragments on a solid support, contacting the immobilized single-stranded deoxyribonucleic acid fragments with a deoxyribonucleic acid probe of claim 12 which includes sites for the incorporation of the oncogene under conditions permitting hybridization of complementary single-stranded molecules, identifying the hybridized molecules so formed to thereby detect abnormalities in the restriction patterns of the chromosomal deoxyribonucleic acid caused by the incorporation of the oncogene into the chromosome.

17. A method as in claim 16, wherein the oncogene is c-abl.

18. A single-stranded deoxyribonucleic acid molecule according to claim 1, which is about 5.8 kb long, is derived from human chromosome 22 and contains sites for incorporation of a deoxyribonucleic acid molecule encoding the oncogene c-abl derived from human chromosome 9 during the Philadelphia translocation.

19. A deoxyribonucleic acid molecule of claim 18 labelled with a detectable marker.

20. A method of diagnosing chronic myelocytic leukemia in a human subject which is associated with an abnormal Philadelphia chromosome containing the translocated oncogene c-abl which comprises cleaving total chromosomal deoxyribonucleic acid with restriction enzymes under cleaving conditions, separating the fragments so obtained by gel electrophoresis, denaturing the fragments to obtain single-stranded deoxyribonucleic acid molecules, recovering the denatured single-stranded fragments from the gel, immobilizing them on a solid support, contacting the immobilized single-stranded deoxyribonucleic acid fragments with a deoxyribonucleic acid probe of claim 19 which includes sites for the incorporation of the chromosome 9 segment containing the oncogene c-abl under conditions permitting hybridization of complementary single-stranded molecules, identifying the hybridized molecules so formed to thereby detect abnormalities in the restriction patterns of the chromosomal deoxyribonucleic acid caused by the presence of the abnormal Philadelphia chromosome.

21. A 1.2 kb fragment of the deoxyribonucleic acid molecule of claim 18 obtained by cleavage with the restriction enzymes Hind III and Bgl II.

22. A fragment of claim 21 labelled with a detectable marker.

23. A method of diagnosing chronic myelocytic leukemia in a human subject which is associated with an abnormal Philadelphia chromosome containing the translocated oncogene c-abl which comprises cleaving total chromosomal deoxyribonucleic acid with restriction enzymes under cleaving conditions, separating the fragments so obtained by gel electrophoresis, denaturing the fragments to obtain single-stranded deoxyribonucleic acid molecules, recovering the denatured single-stranded fragments from the gel, immobilizing them on a solid support, contacting the immobilized single-stranded deoxyribonucleic acid fragments with a 1.2 kb deoxyribonucleic acid probe of claim 22 which includes sites for the incorporation of the chromosome 9 segment containing the oncogene c-abl under conditions permitting hybridization of complementary single-stranded molecules, identifying the hybridized molecules so formed to thereby detect abnormalities in the restriction patterns of the chromosomal deoxyribonucleic acid caused by the presence of the abnormal Philadelphia chromosome.

24. A 0.6 kb fragment of the deoxyribonucleic acid molecule of claim 18 obtained by cleavage with the restriction enzymes Hind III and Bam HI.

25. A fragment of claim 24 labelled with a detectable marker.

26. A method of diagnosing chronic myelocytic leukemia in a human subject which is associated with an abnormal Philadelphia chromosome containing the translocated oncogene c-abl which comprises cleaving total chromosomal deoxyribonucleic acid with restriction enzymes under cleaving conditions, separating the fragments so obtained by gel electrophoresis, denaturing the fragments to obtain single-stranded deoxyribonucleic acid molecules, recovering the denatured single-stranded fragments from the gel, immobilizing them on a solid support, contacting the immobilized single-stranded deoxyribonucleic acid fragments with a 0.6 kb deoxyribonucleic acid probe of claim 25 which includes sites for the incorporation of the chromosome 9 segment containing the oncogene c-abl, under suitable conditions permitting hybridization of complementary single-stranded molecules, identifying the hybridized molecules so formed to thereby detect abnormalities in the restriction patterns of the chromosomal deoxyribonucleic acid caused by the presence of the abnormal Philadelphia chromosome.

* * * * *